(12) United States Patent
Fadel

(10) Patent No.: US 12,324,569 B2
(45) Date of Patent: *Jun. 10, 2025

(54) LARYNGOSCOPE WITH BLADE POSITION ADJUSTMENT

(71) Applicant: Dina Abi Fadel, New York, NY (US)

(72) Inventor: Dina Abi Fadel, New York, NY (US)

( * ) Notice: Subject to any disclaimer, the term of this patent is extended or adjusted under 35 U.S.C. 154(b) by 286 days.

This patent is subject to a terminal disclaimer.

(21) Appl. No.: 16/989,442

(22) Filed: Aug. 10, 2020

(65) Prior Publication Data

US 2020/0367741 A1    Nov. 26, 2020

Related U.S. Application Data

(63) Continuation-in-part of application No. 15/044,112, filed on Feb. 16, 2016, now Pat. No. 10,765,310.

(51) Int. Cl.
   *A61B 17/24* (2006.01)
   *A61B 1/00* (2006.01)
   *A61B 1/04* (2006.01)
   *A61B 1/06* (2006.01)
   *A61B 1/267* (2006.01)

(52) U.S. Cl.
   CPC .......... *A61B 1/267* (2013.01); *A61B 1/00066* (2013.01); *A61B 1/042* (2013.01); *A61B 1/0669* (2013.01)

(58) Field of Classification Search
   CPC ........................................................ A61B 1/267
   USPC ....... 600/185–200, 214, 215, 216, 219, 220, 600/222, 224, 225
   See application file for complete search history.

(56) References Cited

U.S. PATENT DOCUMENTS

| | | | | |
|---|---|---|---|---|
| 2,649,087 A | * | 8/1953 | Allyn ..................... | A61B 1/267 600/196 |
| 5,584,795 A | * | 12/1996 | Valenti ................... | A61B 1/267 600/196 |
| 2003/0181789 A1 | * | 9/2003 | Mazzei .................. | A61B 1/267 600/188 |
| 2006/0247496 A1 | * | 11/2006 | Tjong Joe Wai ...... | A61B 1/267 600/184 |
| 2007/0060794 A1 | * | 3/2007 | Efinger .................. | A61B 1/267 600/219 |
| 2008/0108877 A1 | * | 5/2008 | Bayat ..................... | A61B 1/32 600/245 |

* cited by examiner

*Primary Examiner* — Amy R Sipp
(74) *Attorney, Agent, or Firm* — KALI LAW GROUP, P. C

(57) ABSTRACT

Laryngoscopes are presented including: a handle having a front side, a proximal end, and a distal end; a blade movably coupled to the handle and projecting from the front side of the handle proximate the distal end of the handle; and a mechanism for moving the blade relative to the handle, where the mechanism is responsive to manual input by a user, the mechanism further including: a guide linkage constraining the blade to move in at least one predetermined path relative to the handle, where the first predetermined path includes a first designated path traveled on a flat plane by the blade, the flat plane simultaneously bisecting a handle length and a blade length, where during the travel an angle between the handle length and the blade length remains constant while the blade translates along the handle length.

18 Claims, 7 Drawing Sheets

LARYNGOSCOPE WITH BLADE POSITION ADJUSTMENT

FIELD OF INVENTION

The present invention relates to laryngoscopes, and more particularly, to a laryngoscope having a blade repositionable relative to the handle.

BACKGROUND

Laryngoscopes are used to reposition body organs such as the tongue, for example, to prepare for intubation during medical procedures. A laryngoscope is grasped by and manually manipulated to achieve desired reposition of the body organs. However, a considerable force may be necessary to achieve the desired repositioning. Application of such force may risk injury to both the patient and, also potentially, the operator. Appropriate positioning of the laryngoscope is critical for successful intubation.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented below.

As such laryngoscopes are presented including: a handle having a front side, a proximal end, and a distal end; a blade movably coupled to the handle and projecting from the front side of the handle proximate the distal end of the handle; and a mechanism for moving the blade relative to the handle, where the mechanism is responsive to manual input by a user, the mechanism further including: a guide linkage constraining the blade to move in at least one predetermined path relative to the handle, where the at least one predetermined path is selected from a group consisting of: a first predetermined path, where the first predetermined path includes a first designated path traveled on a flat plane by the blade, the flat plane simultaneously bisecting a handle length and a blade length, where during the travel an angle between the handle length and the blade length remains constant while the blade translates along the handle length, a second predetermined path where the second predetermined path includes a second designated path traveled on a flat plane by the blade, the flat plane simultaneously bisecting a handle length and a blade length, where the blade pivots about a fulcrum positioned on the flat plane where the handle and the blade intersect, the pivoting causing a number of inclination angles between the blade length and the handle length on the flat plane, a third predetermined path where the third predetermined path includes a third designated path traveled on a flat plane by the blade, the flat plane simultaneously bisecting the handle along a substantially widthwise direction thereof and a blade length, where during the travel the blade pivots about an axis through the handle length while maintaining a constant angle to the handle, and a fourth predetermined path extending transversely relative to a length of the handle, where the fourth predetermined path further includes a fourth designated path traveled on a flat plane by the blade, the flat plane simultaneously bisecting a handle length and a blade length, where during the travel an angle between the handle length and the blade length remains constant while the blade moves transversely toward or away from an axis through a center of the blade. In some embodiments, the mechanism further includes a finger actuated turn knob or a finger actuated slider.

In other embodiments, laryngoscopes are presented including: a handle having a front side, a proximal end, and a distal end; a blade movably coupled to the handle and projecting from the front side of the handle proximate the distal end of the handle; and a mechanism for moving the blade relative to the handle, where the mechanism is responsive to manual input by a user, the mechanism further including: a guide linkage constraining the blade to move in a designated path traveled on a flat plane by the blade, the flat plane simultaneously bisecting a handle length and a blade length, where during the travel an angle between the handle length and the blade length remains constant while the blade translates along the handle length.

In other embodiments, laryngoscopes are presented including: a handle having a front side, a proximal end, and a distal end; a blade movably coupled to the handle and projecting from the front side of the handle proximate the distal end of the handle; and a mechanism for moving the blade relative to the handle, where the mechanism is responsive to manual input by a user, the mechanism further including: a guide linkage constraining the blade to move in a designated path traveled on a flat plane by the blade, the flat plane simultaneously bisecting a handle length and a blade length, where the blade pivots about a fulcrum positioned on the flat plane where the handle and the blade intersect, the pivoting causing a number of inclination angles between the blade length and the handle length on the flat plane.

In other embodiments, laryngoscopes are presented including: a handle having a front side, a proximal end, and a distal end; a blade movably coupled to the handle and projecting from the front side of the handle proximate the distal end of the handle; and a mechanism for moving the blade relative to the handle, where the mechanism is responsive to manual input by a user, the mechanism further including: a guide linkage constraining the blade to move in a designated path traveled on a flat plane by the blade, the flat plane simultaneously bisecting the handle along a substantially widthwise direction thereof and a blade length, where during the travel the blade pivots about an axis through the handle length while maintaining a constant angle to the handle.

In other embodiments, laryngoscopes are presented including: a handle having a front side, a proximal end, and a distal end; a blade movably coupled to the handle and projecting from the front side of the handle proximate the distal end of the handle; and a mechanism for moving the blade relative to the handle where the mechanism is responsive to manual input by a user, the mechanism further including: a guide linkage constraining the blade to move in a designated path traveled on a flat plane by the blade, the flat plane simultaneously bisecting a handle length and a blade length, during the travel an angle between the handle length and the blade length remains constant while the blade moves transversely toward or away from an axis through a center of the blade.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

The present invention will now be described in detail with reference to a few embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

In still other instances, specific numeric references such as "first material," may be made. However, the specific numeric reference should not be interpreted as a literal sequential order but rather interpreted that the "first material" is different than a "second material." Thus, the specific details set forth are merely exemplary. The specific details may be varied from and still be contemplated to be within the spirit and scope of the present disclosure. The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

Figure 1:
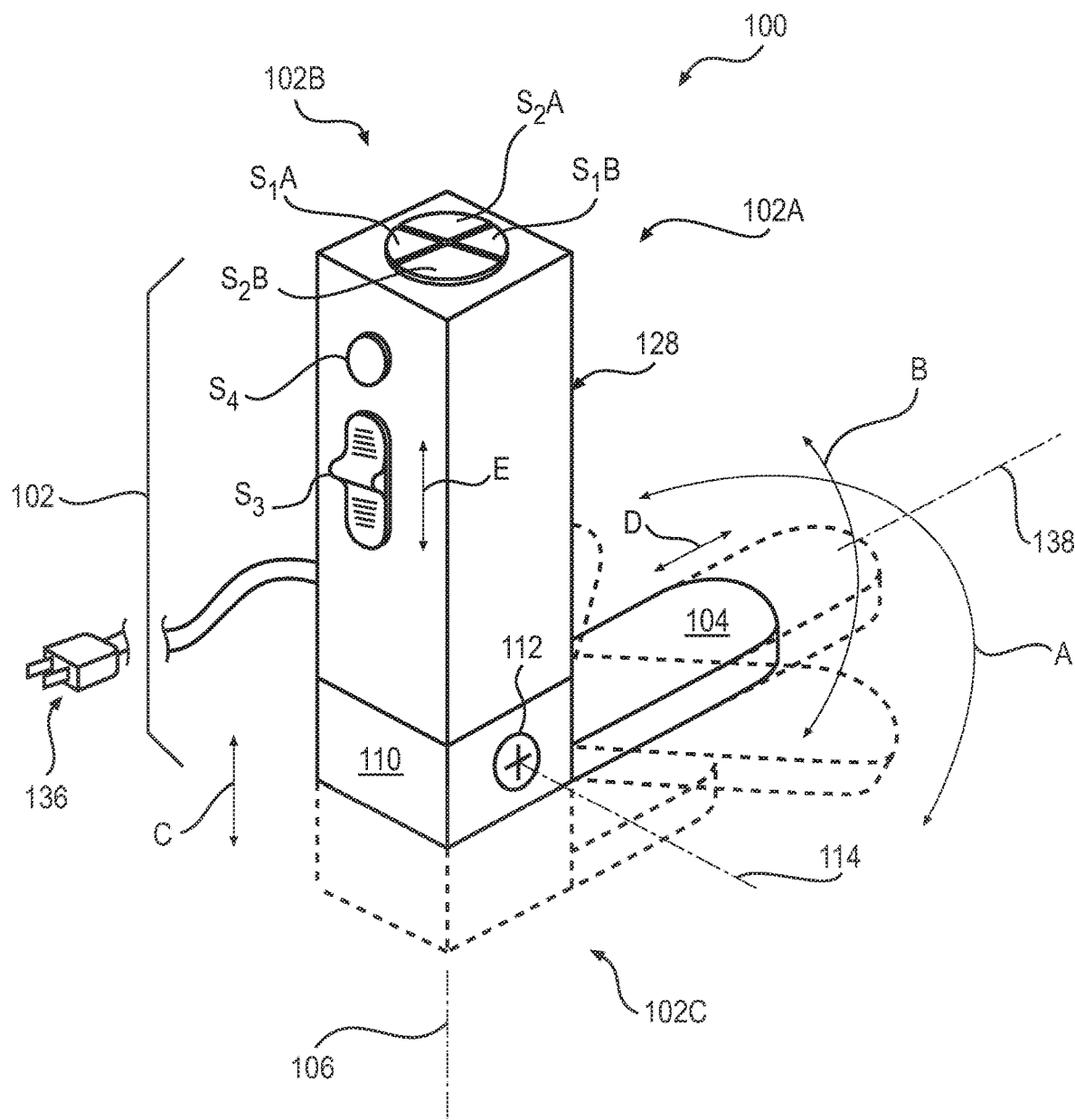
FIG. 1 is a diagrammatic perspective view of a laryngoscope, according to at least one aspect of the disclosure.

Referring first to FIG. 1, according to at least one aspect of the disclosure, there is shown a laryngoscope 100 comprising a handle 102 having a front side 102A, a proximal end 102B, and a distal end 102C, a blade 104 movably coupled to handle 102 and projecting from the front side 102A and proximate distal end 102C of handle 102, and a mechanism, such as one or more motors and one or more gears, for moving blade 104 relative to handle 102. The front side 102A may comprise, for example, a flat surface thereby providing a front side to handle 102, a rounded surface thereby providing a front face to handle 102, a dimple surface, a ridged surface or any suitable grip surface made up of, for example, ridges to provide a grip surface; in short, front side 102A is not limited to a particular overall shape or appearance. Blade 104 is that portion of laryngoscope 100 which contacts and lifts the tongue or other body tissue (none shown) being manipulated by medical personnel. Handle 102 has length along axis 102D. In FIG. 1, four positional adjustments are represented. Representative alternative positions of blade 104 relative to handle 102 are indicated in broken lines throughout FIGS. 1-5.

For semantic convenience in explaining these positional adjustments, laryngoscope 100 is shown in what will be called an upright position of use. It should be noted at this point that orientational terms such as upright, right, and left, etc., refer to the subject drawing as viewed by an observer. The subject matter could obviously change depending on orientation of the user's hand. Therefore, orientational terms must be understood to provide semantic basis for purposes of description only, and do not imply that their subject matter can be used only in one position.

The mechanism for moving blade 104 relative to handle 102 may comprise, for example, at least one electric motor, and a linkage arranged to move or guide blade 104 responsive to operation of the at least one motor.

The present invention is not limited to a specific type of laryngoscope. For example, the laryngoscope 100 can comprise a non-flexible or flexible handle 102.

Figure 2:
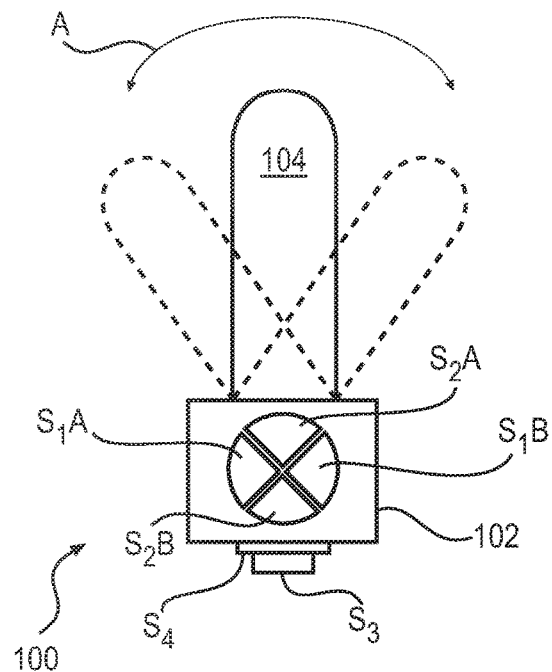
FIG. 2 is a diagrammatic top plan view of the laryngoscope of FIG. 1, according to at least one aspect of the disclosure.
Figure 6:
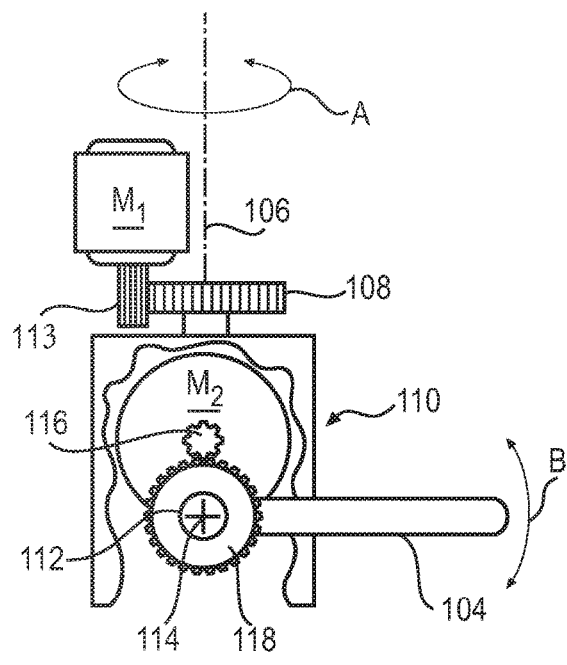
FIG. 6 is a diagrammatic side detail view of internal components of the laryngoscope of FIG. 1, according to at least one aspect of the disclosure.

Referring also to FIG. 2, blade 104 is pivotally movable to the right and to the left (this right-and-left motion is indicated by arrow A) with respect to axis 106 extending along the length of handle 102 (FIG. 6). Blade 104 is moved as desired along the path indicated by arrow A. This movement is initiated by pushbutton switch S1. Switch S1 comprises two pushbutton switches S1A and S1B. Switches S1A and S1B are arranged to alternate polarities of DC current applied to motor M1 (see FIG. 6) as well as making and breaking circuitry (see FIG. 9) serving motor M1, the latter reversibly effecting movement of blade 104 along the path indicated by arrow A, as will be further explained hereinafter.

Blade 104 may be configured in ways other than as depicted in the drawing figures. For example, blade 104 may be curved, straight, or may be configured to cooperate with the anatomy.

Handle 102 and blade 104 may be provided as integral with one another, or alternatively, may be separable.

For the purposes of this disclosure, switches are depicted as switch operators only (e.g., pushbuttons or slider), but may include contacts and other switch components. Additionally, it should be understood that switches may be located other than where depicted herein.

Right and left movement of blade 104 relative to longitudinal axis 106 (FIG. 6), is accomplished by rotating a gear 108 fixed to a cartridge 110 containing an axle 112 on which blade 104 is pivotally mounted to pivot about axis 114. Cartridge 110 is movably contained within handle 102 to accommodate additional adjustments to be described hereinafter.

Motor M1 has a splined output shaft 113 geared to gear 108 fixed to cartridge 110. Operation of motor M1 therefore rotates cartridge 110 and hence blade 104 within handle 102 (FIG. 1) about axis 106.

Figure 3:
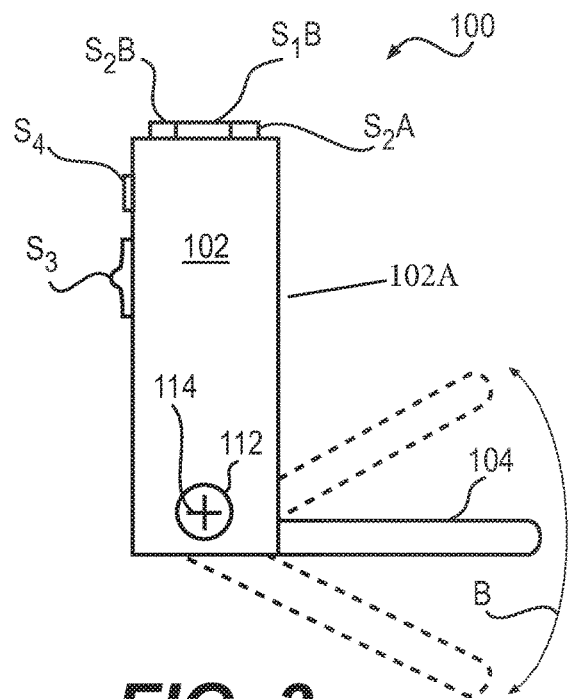
FIG. 3 is a diagrammatic side view of the laryngoscope of FIG. 1, illustrating one powered positional adjustment of the blade, according to at least one aspect of the disclosure.

Referring to FIGS. 1, 3, and 6, blade 104 may be pivotally moved through a vertical path indicated by arrow B to vary an angle between blade 104 and axis 106 of handle 102. This movement is effected by pushbutton switch S2 comprising switches S2A and S2B (FIG. 1). Switches S2A, S2B alternate polarities of DC current applied to motor M2 (FIG. 6) as well as making and breaking circuitry (FIG. 9) serving motor M2. Motor M2 rotates a splined output shaft 116 (seen in end view in FIG. 6) geared to a gear 118.

Figure 4:
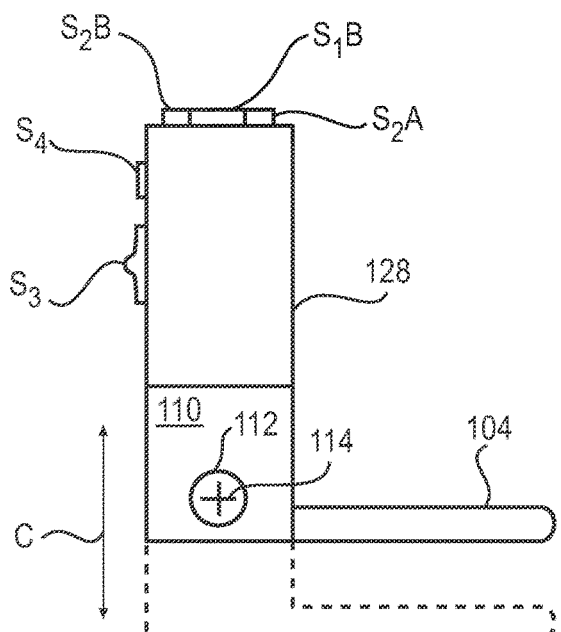
FIG. 4 is a diagrammatic side view of the laryngoscope of FIG. 1, illustrating another powered positional adjustment of the blade, according to at least one aspect of the disclosure.
Figure 7:
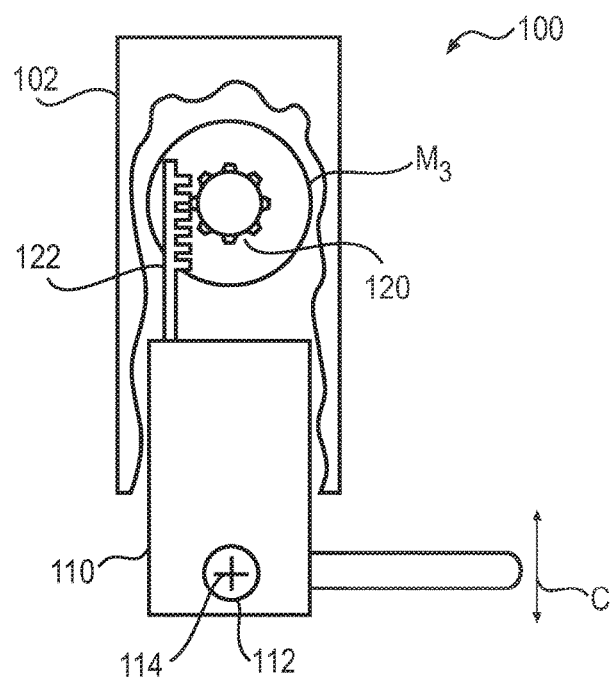
FIG. 7 is a diagrammatic side detail view of internal components of the laryngoscope of FIG. 1, broken away to reveal other internal components, according to at least one aspect of the disclosure.

Referring to FIGS. 1, 4, and 7, blade 104 may be moved along the length of handle 102, as indicated by arrow C. This movement is effected by a sliding switch S3. Sliding switch S3 both alternates polarities of DC current applied to motor M3 (FIG. 7), as well as making and breaking circuitry (FIG. 9) serving motor M3. Referring specifically to FIG. 7, motor M3 has a splined output shaft 120 (seen in end view in FIG. 7) engaging a toothed rack 122 fixed to cartridge 110. Hence operation of motor M3 causes cartridge 110 and blade 104 to translate along handle 102, as indicated by arrow C.

Figure 5:
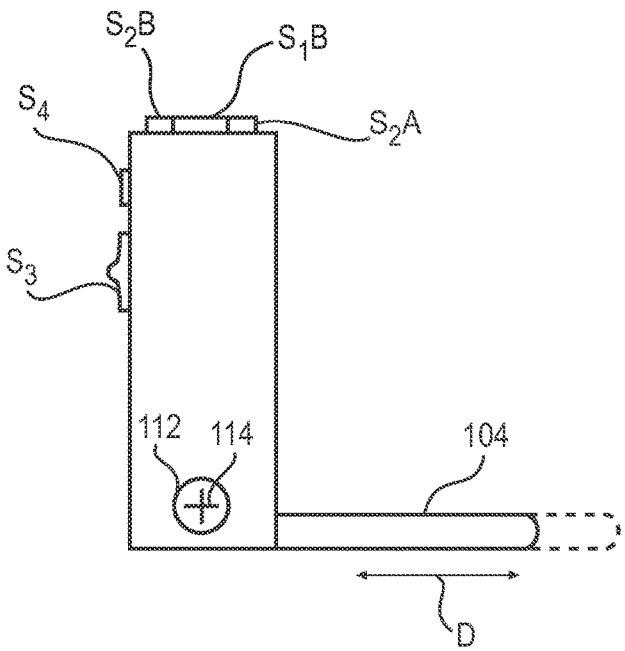
FIG. 5 is a diagrammatic side view of the laryngoscope of FIG. 1, illustrating still a further powered positional adjustment of the blade, according to at least one aspect of the disclosure.
Figure 8:
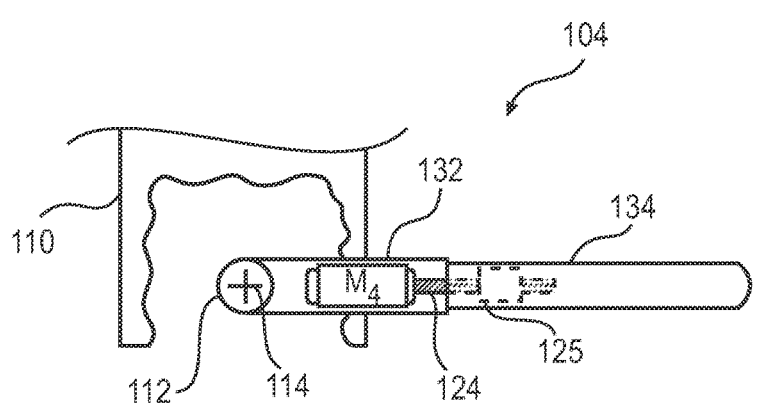
FIG. 8 is a diagrammatic side detail view of internal components of the laryngoscope of FIG. 1, broken away to reveal still other internal components, according to at least one aspect of the disclosure.

Referring to FIGS. 1, 5, and 8, it is also possible to vary exposed length of blade 104 by a switch S4. Switch S4 operates by toggle logic. That is, alternating usages of switch S4 reverse polarity of current applied to motor M4. As seen in FIG. 8, motor M4 has a threaded output shaft 124 engaging a nut 125 held captive and constrained against rotation in telescoping section 132 of blade 104. Rotation of threaded output shaft 124 causes telescoping section 132 to translate along blade 104. Reversible extension 128 of blade 104, indicated by arrow D in FIG. 5, is thereby accomplished by motor M4.

The various motions of blade 104 indicated by arrows A, B, C, and D may be regarded as discrete possible motions of blade 104. One dedicated switch S1, S2, S3, or S4 reversibly controls each one of the discrete possible motions. Therefore, blade 104 has at least two discrete possible motions and a switch (S1, S2, S3, or S4) reversibly controlling each one of the at least two discrete motions.

Laryngoscope 100 further comprises a guide linkage constraining blade 104 to move in at least one predetermined path relative to handle 102. Laryngoscope 100 includes at least one motor M1, M2, M3, or M4 in handle 100, the at least one motor M1, M2, M3, or M4 housed in the handle, having a motion output when the motor M1, M2, M3, or M4 is operating. Laryngoscope 100 includes at least one transmission for each one of the at least one motor M1, M2, M3, or M4, which said at least one transmission moves blade 104 in one of the at least one predetermined path responsive to operation of at least one motor M1, M2, M3, or M4.

The predetermined path may comprise a first predetermined path wherein blade 104 inclines at different angles relative to the length of handle 102 in a plane occupied by a longitudinal center line 106 of handle 102 and a longitudinal center line 138 (FIG. 1) of blade 104. The first predetermined path is illustrated in FIG. 3.

The predetermined path may comprise a second predetermined path wherein blade 104 pivots about axis 106 parallel to the length of handle 102. The second predetermined path lies in a plane perpendicular to longitudinal center line 106 of handle 102, as shown in FIG. 2.

The predetermined path may further comprise a third predetermined path along a plane passing through handle 102, wherein an angle between the plane and blade 104 is constant while blade 104 moves along the plane The third predetermined path is illustrated in FIG. 4.

The predetermined path may further comprise a fourth predetermined path extending transversely relative to the length of handle 102, wherein an angle between the handle and blade 104 remains constant while blade 104 moves transversely relative to handle 102. The fourth predetermined path is illustrated in FIG. 5.

The predetermined path may comprise a first predetermined path wherein blade 104 inclines at different angles relative to the handle 102 of blade 104; a second predetermined path wherein blade 104 pivots about an axis parallel to the length of handle 102; a third predetermined path along the length of handle 102, wherein an angle between handle 102 and blade 104 remains constant while blade 104 moves along a plane extending through handle 102; and a fourth predetermined path extending transversely relative to the length of handle 102, wherein an angle between handle 102 and blade 104 remains constant while blade 104 moves transversely relative to handle 102. If desired, any combination of the predetermined paths described herein may be incorporated into the novel laryngoscope 100.

A transmission is a linkage which transmits motor output to blade 104 and adapts the motor output to effect the appropriate movement of blade 104. In the example of FIG. 6, gear 108 and splined output shaft 116 provide the transmission for accomplishing the movement illustrated in FIG. 2. Also in FIG. 6, axle 112 and splined output shaft 116 provide the transmission for accomplishing the movement illustrated in FIG. 3. In FIG. 7, splined output shaft 120 and toothed rack 122 provide the transmission accomplishing the movement illustrated in FIG. 4. In FIG. 8, threaded output shaft 124 and nut 125, the latter fixed to blade 104, provide the transmission for accomplishing the movement illustrated in FIG. 5.

The structure constraining the blade to move as described is provided by engagement or entrapment of a moved component by a portion of handle 102. For example, an outer housing 128 of handle 102 surrounds cartridge 110, constraining the latter to move in the direction of arrow C when blade 104 moves as illustrated in FIG. 4. Correspondingly, axle 112 is journaled within cartridge 110 such that blade 104 pivots as shown by arrow B in FIGS. 1 and 6. In FIG. 8, projection of a distal telescoping section 134 of blade 104 is guided and constrained by close sliding cooperation with telescoping section 132.

Laryngoscope 100 comprises an electrical power source, electrical circuitry connected to the electrical power source and the at least one motor M1, M2, M3, or M4, and at least one switch S1, S2, S3, or S4 on an exterior of handle 102 for each at least one motor M1, M2, M3, or M4. Each at least one switch S1, S2, S3, S4 is arranged to make and break power from the electrical power source to the at least one motor M1, M2, M3, or M4. The electrical power source comprises battery 130 in handle 102. Alternatively, or in addition to battery 130, where the latter is a rechargeable battery 130, the power source may be a plug and cord assembly 136 (FIG. 1). The plug and cord assembly is connected to the electrical circuitry to enable operation as described herein. Where battery 130 is provided as a rechargeable battery 130, it will be understood to include an AC-to-DC converter and other components required for operability as described herein.

In one implementation of the disclosure, the at least one motor comprises first motor M1 arranged to move blade 104 along the first predetermined path, and the at least one transmission comprises a first transmission arranged to move blade 104 in the first predetermined path responsive to operation of first motor M1, and first switch S1 on handle 102, first switch S1 arranged to make and break power from the electrical circuitry to first motor M1. The at least one motor comprises second motor M2 arranged to move blade 104 along the second predetermined path, and the at least one transmission comprises a second transmission arranged to move blade in the second predetermined path responsive to operation of second motor M2, and second switch S2 on handle 102, second switch S2 arranged to make and break power from the electrical circuitry to second motor M2. The at least one motor comprises third motor M3 arranged to move blade 104 along the third predetermined path, and the at least one transmission comprises a third transmission arranged to move blade 104 in the third predetermined path responsive to operation of third motor M3, and third switch S3 on handle 102, third switch S3 arranged to make and break power from the electrical circuitry to third motor M3. The at least one motor comprises fourth motor M4 arranged to move blade 104 along the fourth predetermined path, and the at least one transmission comprises a fourth transmission arranged to move blade 104 in the fourth predetermined path responsive to operation of fourth motor M4, and fourth switch S4 on handle 102, the fourth switch arranged to make and break power from the electrical circuitry to fourth motor M4.

In an implementation of the disclosure, first switch S1 comprises a first sub-switch SIA arranged to operate first motor M1 in a first direction, and a second sub-switch SIB arranged to operate first motor M1 in an opposed direction. Second switch S2 comprises a third sub-switch S2A arranged to operate second motor M2 in a first direction, and a fourth sub-switch S2B arranged to operate second motor M2 in an opposed direction.

In the above implementation, first sub-switch SIA, second sub-switch SIB, third sub-switch S2A, and fourth sub-switch S2B are in an array wherein each one of first sub-switch SIA, second sub-switch SIB, third sub-switch S2A, and fourth sub-switch S2B is adjacent to two others of first sub-switch SIA, second sub-switch SIB, third sub-switch S2A, and fourth sub-switch S2B. First sub-switch SIA is opposite second sub-switch SIB in the array, and third sub-switch S2A is opposite fourth sub-switch S2B in the array. This is shown in FIG. 1.

In an implementation of the disclosure, third switch S3 is a slide action switch movable in opposed directions to operate third motor M3 selectively in respective opposed directions. In FIG. 1, the opposed directions are indicated by an arrow E.

Figure 10:
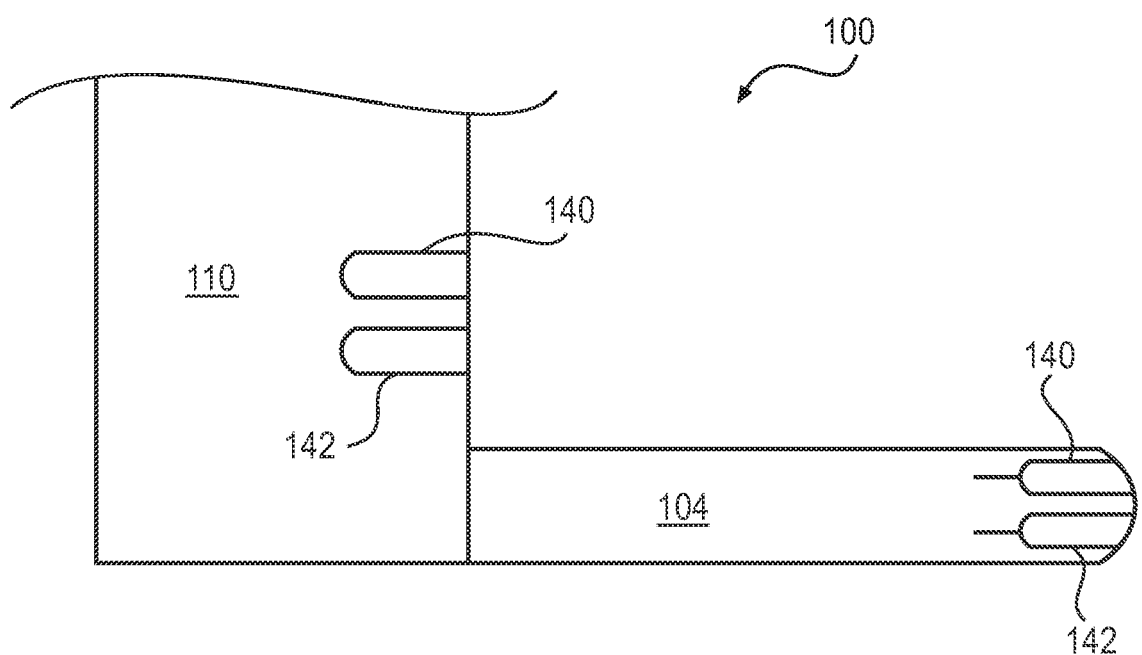
FIG. 10 is a side detail view of optional components of the laryngoscope of FIG. 1, according to at least one aspect of the disclosure.

Optionally, and referring to FIG. 10, laryngoscope 100 comprises a light source 140 operable to project light from laryngoscope 100. In one option, light source 140 is in handle 102. In another option, light source 140 is in blade 104.

In a further option, which may be executed with or without the option for light source 140, laryngoscope 100 further comprises a camera 142 operable to record the environment of blade 104. In laryngoscope 100, camera 142 is in handle 102. Alternatively or in addition to a camera 142 in handle 102, in laryngoscope 100, camera 142 is in blade 104. Power and signals may be conducted in electrical or optic fiber cables (none shown) passing through blade 104 or handle 102, as appropriate.

Mechanical linkages imparting motion to blade 104 from motors M1, M2, M3, and M4 as described above (i.e., splined output shafts 114, 116, 120, and 124, and their associated driven elements), which form a mechanism for moving blade 104 relative to handle 102 may be varied in their nature from the arrangements shown and described herein. For example, linear motors (not shown) rather than rotary output motors may be incorporated into laryngoscope 100.

Location and nature of switches S1, S2, S3 or S4 and their pushbutton operators may be varied from the arrangements shown and described herein.

Figure 9:
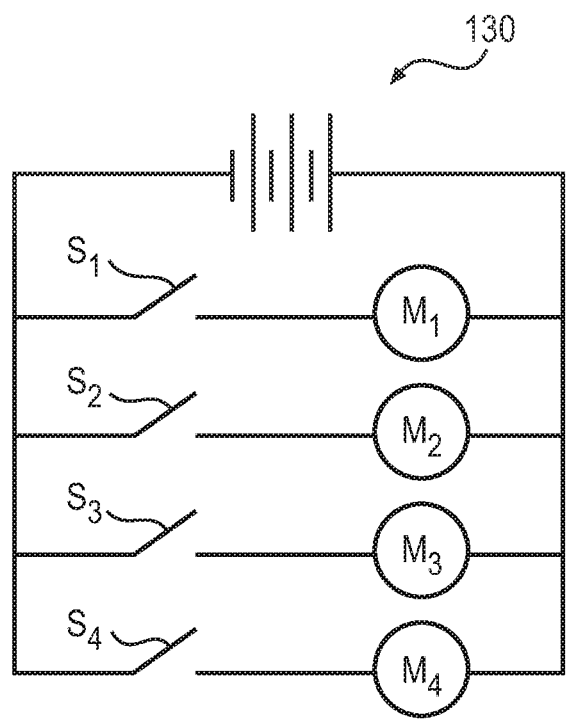
FIG. 9 is an electrical schematic showing a power and control circuit of the laryngoscope of FIG. 1.

FIG. 9 shows power circuitry serving motors M1, M2, M3, and M4. Battery 130 is contained within handle 102. As an alternative, laryngoscope 100 may have a power cord (not shown) for connection to AC power, and an AC-to-DC converter (not shown) in place of battery 130. In a further alternative, laryngoscope 100 may have both an AC power connection with a converter (neither shown), and also a rechargeable battery 130.

As an alternative to electrically powered operation, some positional adjustments of blade 104 may be mechanically accomplished. For example, linkages (not shown) incorporating pusher rods, levers, and rocker arms may be employed where feasible. Functions of laryngoscope 100 described herein in terms of electrical power may in alternative realizations of the disclosure be accomplished mechanically as disclosed below for FIGS. 11-15. Piston and cylinder assemblies and other known mechanical arrangements, and pneumatic and/or hydraulic systems may be incorporated, for example.

Although handle 102 has been depicted as a parallelepiped, handle 102 may be rounded, flat and straight, curved, or may reflect oral cavity anatomy. Handle 102 may incorporate a recess or alternatively, an outwardly projecting wall (neither shown) to help direct the endotracheal tube passage towards the larynx.

Figures 11A, 11B:
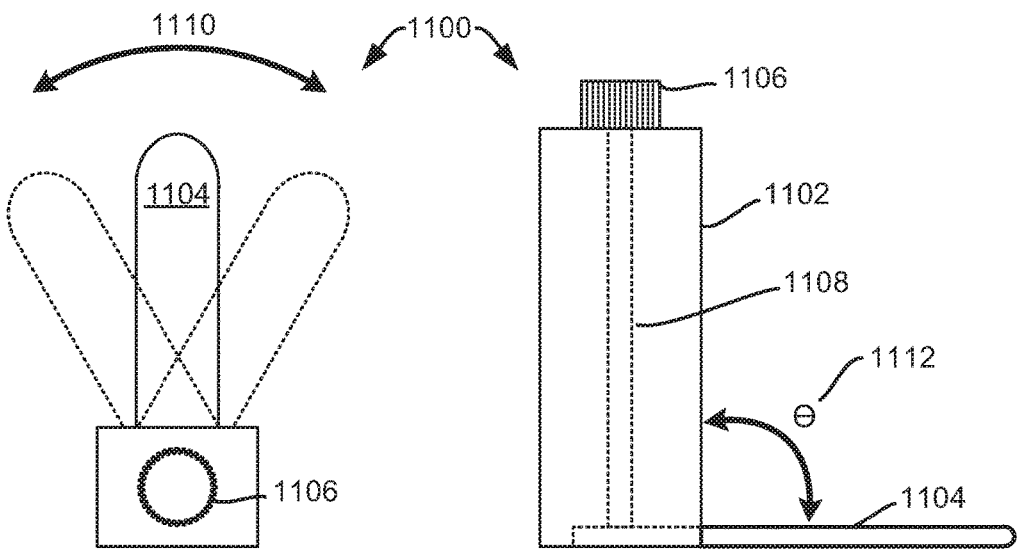
FIGS. 11A-B are illustrative representations of a mechanically actuated laryngoscope in accordance with embodiments of the present invention.

FIGS. 11A-B are illustrative representations of a mechanically actuated laryngoscope in accordance with embodiments of the present invention. In particular, FIG. 11A is a top view of mechanically actuated laryngoscope 1100 and FIG. 11B is a side view of mechanically actuated laryngoscope 1100. As illustrated, mechanically actuated laryngoscope 1100 includes handle 1102 that includes a front side from which extends blade 1104, a proximal end from which blade 1104 extends, and a distal end where finger actuated turn knob 1106 is located. In use, finger actuated turn knob embodiments may be manipulated by one or more fingers such that the mechanism is responsive to manual input by a user. When the finger actuated knob is actuated, guide linkage 1108 constrains blade 1104 to move in a predetermined and designated path traveled on a flat plane by the blade as indicated by arrow 1110. As illustrated, the flat plane simultaneously bisects the handle along a substantially widthwise direction thereof and the blade length. During travel, the blade pivots about an axis through the handle length while maintaining a constant angle (1112) to the handle.

Figures 12A, 12B:
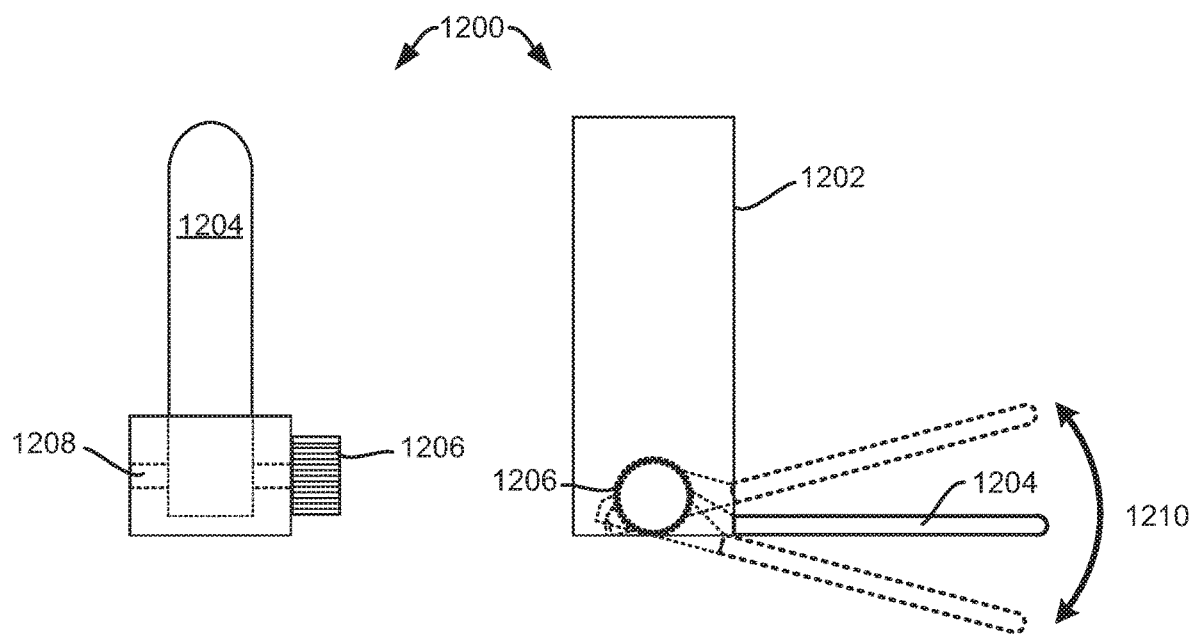
FIGS. 12A-B are illustrative representations of a mechanically actuated laryngoscope in accordance with embodiments of the present invention.

FIGS. 12A-B are illustrative representations of a mechanically actuated laryngoscope in accordance with embodiments of the present invention. In particular, FIG. 12A is a top view of mechanically actuated laryngoscope 1200 and FIG. 12B is a side view of mechanically actuated laryngoscope 1200. As illustrated, mechanically actuated laryngoscope 1200 includes handle 1202 that includes a front side from which extends blade 1204, a proximal end from which blade 1204 extends and where finger actuated turn knob 1206 is located. In use, finger actuated turn knob embodiments may be manipulated by one or more fingers such that the mechanism is responsive to manual input by a user. When the finger actuated knob is actuated, guide linkage 1208 constrains blade 1204 to move in a predetermined and designated path traveled on a flat plane by the blade as indicated by arrow 1210. As illustrated, the flat plane simultaneously bisects the handle length and the blade length. During travel, the blade pivots about a fulcrum positioned on the flat plane where the handle and the blade intersect. The pivoting causes various inclination angles between the blade length and the handle length on the flat plane.

Figures 13A, 13B:
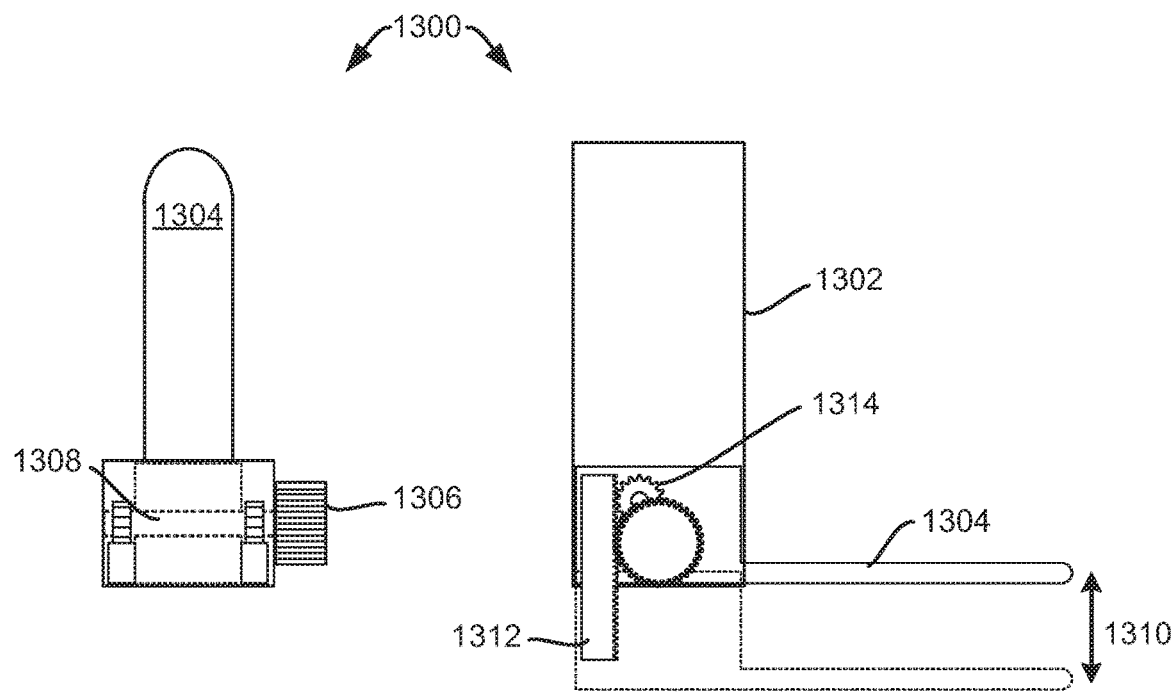
FIGS. 13A-B are illustrative representations of a mechanically actuated laryngoscope in accordance with embodiments of the present invention.

FIGS. 13A-B are illustrative representations of a mechanically actuated laryngoscope in accordance with embodiments of the present invention. In particular, FIG. 13A is a top view of mechanically actuated laryngoscope 1300 and FIG. 13B is a side view of mechanically actuated laryngoscope 1300. As illustrated, mechanically actuated laryngoscope 1300 includes handle 1302 that includes a front side from which extends blade 1304, a proximal end from which blade 1304 extends and where finger actuated turn knob 1306 is located. In use, finger actuated turn knob embodiments may be manipulated by one or more fingers such that the mechanism is responsive to manual input by a user. When the finger actuated knob is actuated, guide linkage 1308 constrains blade 1304 to move in a predetermined and designated path traveled on a flat plane by the blade as indicated by arrow 1310. The mechanism illustrated includes rack 1312 and pinion 1314 elements to effect the desired movement. As illustrated, the flat plane simultaneously bisects the handle length and the blade length. During travel, an angle between the handle length and the blade length remains constant while the blade translates along the handle length as indicated by arrow 1310.

Figures 14A, 14B:
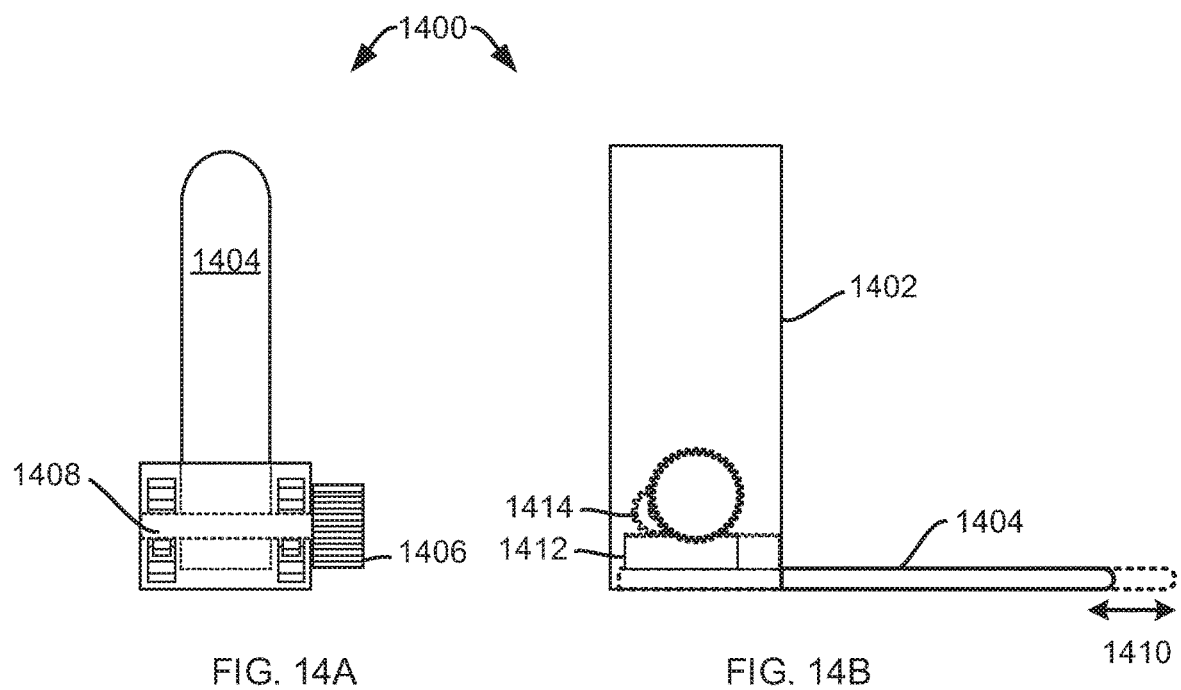
FIGS. 14A-B are illustrative representations of a mechanically actuated laryngoscope in accordance with embodiments of the present invention.

FIGS. 14A-B are illustrative representations of a mechanically actuated laryngoscope in accordance with embodiments of the present invention. In particular, FIG. 14A is a top view of mechanically actuated laryngoscope 1400 and FIG. 14B is a side view of mechanically actuated laryngoscope 1400. As illustrated, mechanically actuated laryngoscope 1400 includes handle 1402 that includes a front side from which extends blade 1404, a proximal end from which blade 1404 extends and where finger actuated turn knob 1406 is located. In use, finger actuated turn knob embodiments may be manipulated by one or more fingers such that the mechanism is responsive to manual input by a user. When the finger actuated knob is actuated, guide linkage 1408 constrains blade 1404 to move in a predetermined and designated path traveled on a flat plane by the blade as indicated by arrow 1410. The mechanism illustrated includes rack 1412 and pinion 1414 elements to effect the desired movement. As illustrated, the flat plane simultaneously bisects the handle length and the blade length. During travel, an angle between the handle length and the blade length remains constant while the blade moves transversely toward or away from an axis through a center of the blade as indicated by arrow 1410.

Figures 15A, 15B:
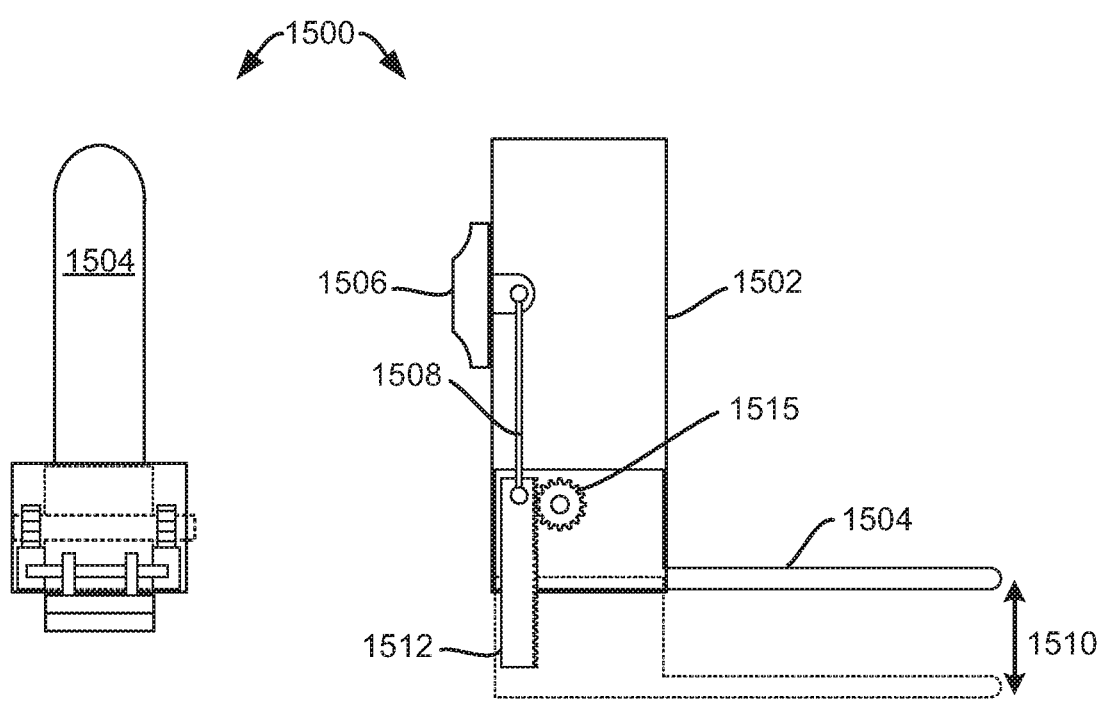
FIGS. 15A-B are illustrative representations of a mechanically actuated laryngoscope in accordance with embodiments of the present invention.

FIGS. 15A-B are illustrative representations of a mechanically actuated laryngoscope in accordance with embodiments of the present invention. In particular, FIG. 15A is a top view of mechanically actuated laryngoscope 1500 and FIG. 15B is a side view of mechanically actuated laryngoscope 1500. As illustrated, mechanically actuated laryngoscope 1500 includes handle 1502 that includes a front side from which extends blade 1504, a proximal end from which blade 1504 extends, and a distal end where finger actuated slider 1506 is located. In use, finger actuated slider embodiments may be manipulated by one or more fingers such that the mechanism is responsive to manual input by a user. When the finger actuated slider is actuated, guide linkage 1508 constrains blade 1504 to move in a predetermined and designated path traveled on a flat plane by the blade as indicated by arrow 1510. The mechanism illustrated includes rack 1512 and pinion 1514 elements to effect the desired movement. As illustrated, the flat plane simultaneously bisects the handle length and the blade length. During travel, an angle between the handle length and the blade length remains constant while the blade translates along the handle length as indicated by arrow 1510.

FIGS. 11-15 illustrated various manual mechanisms by which mechanically actuated laryngoscope embodiments may be operated. The illustrations are provided to show various mechanism that are responsive to manual input by a user and should not be construed as limiting with respect to mechanisms well-known in the art. Indeed, any number of mechanical elements may be utilized to provide the movements enabled by the mechanically actuated laryngoscope embodiments disclosed herein. In addition, in embodiments, mechanical elements may be combined without limitation to provide two or more different movements.

The terms "certain embodiments", "an embodiment", "embodiment", "embodiments", "the embodiment", "the embodiments", "one or more embodiments", "some embodiments", and "one embodiment" mean one or more (but not all) embodiments unless expressly specified otherwise. The terms "including", "comprising", "having" and variations thereof mean "including but not limited to", unless expressly specified otherwise. The enumerated listing of items does not imply that any or all of the items are mutually exclusive, unless expressly specified otherwise. The terms "a", "an" and "the" mean "one or more", unless expressly specified otherwise.

While this invention has been described in terms of several embodiments, there are alterations, permutations, and equivalents, which fall within the scope of this invention. It should also be noted that there are many alternative ways of implementing the methods and apparatuses of the present invention. Furthermore, unless explicitly stated, any method embodiments described herein are not constrained to a particular order or sequence. Further, the Abstract is provided herein for convenience and should not be employed to construe or limit the overall invention, which is expressed in the claims. It is therefore intended that the following appended claims be interpreted as including all such alterations, permutations, and equivalents as fall within the true spirit and scope of the present invention.

What is claimed is:

1. A laryngoscope comprising:
   a handle having a handle length, a front side, a proximal end, and a distal end;
   a single blade movably coupled to the handle and projecting from the front side of the handle proximate the distal end of the handle, the single blade having a blade length; and
   a mechanism for moving the single blade relative to the handle, wherein the mechanism is responsive to manual input by a user, the mechanism further comprising:
   a guide linkage constraining the single blade to move in at least one combination of predetermined paths relative to the handle, wherein the at least one combination of predetermined paths is selected from a group consisting of:
   a first predetermined path, wherein the first predetermined path comprises a first designated path traveled along a first plane by the single blade, the first plane vertically bisecting the handle, wherein during the travel an angle between the handle length and the single blade length remains constant while the single blade translates along a handle length axis,
   a second predetermined path, wherein the second predetermined path comprises a second designated path traveled along a first plane by the single blade, wherein the single blade pivots axially about a fulcrum, wherein the fulcrum is positioned proximate to and coaxial with a turn knob shaft housed within the handle, wherein the pivoting causes a plurality of inclination angles between the blade length and the handle length, and wherein the turn knob shaft is substantially perpendicular to the handle length,
   a third predetermined path, wherein the third predetermined path comprises a third designated path traveled along a second plane by the single blade, the second plane horizontally bisecting the blade length, wherein during the travel the blade pivots axially about a handle axis while maintaining a constant angle with respect to the handle,
   a fourth predetermined path extending transversely relative to the handle length, wherein the fourth predetermined path further comprises a fourth designated path traveled along a second plane by the single blade, wherein during the travel an angle between the handle length and the blade length remains constant while the single blade moves transversely toward or away from the handle length.

2. The laryngoscope of claim 1 wherein the mechanism further comprises a finger actuated turn knob positioned at one end of the turn knob shaft.

3. The laryngoscope of claim 1 wherein the mechanism further comprises a finger actuated slider.

4. The laryngoscope of claim 1, further comprising a light source operable to project light from the laryngoscope.

5. The laryngoscope of claim 4, wherein the light source is in the handle.

6. The laryngoscope of claim 4, wherein the light source is in the blade.

7. The laryngoscope of claim 1, further comprising a camera operable to record an environment of the blade.

8. The laryngoscope of claim 7, wherein the camera is in the handle.

9. The laryngoscope of claim 7, wherein the camera is in the blade.

10. A laryngoscope comprising:
    a handle having a handle length, a front side, a proximal end, and a distal end;
    a single blade movably coupled to the handle and projecting from the front side of the handle proximate the distal end of the handle, the single blade having a blade length; and
    a mechanism for moving the single blade relative to the handle, wherein the mechanism is responsive to manual input by a user, the mechanism further comprising:
    a guide linkage constraining the single blade to move in at least two predetermined paths relative to the handle, wherein the at least two predetermined paths are selected from a group consisting of:
    a first predetermined path, wherein the first predetermined path comprises a first designated path traveled along a first plane by the single blade, the first plane vertically bisecting the handle, wherein during the travel an angle between the handle length and the single blade length remains constant while the single blade translates along a handle length axis,
    a second predetermined path, wherein the second predetermined path comprises a second designated path traveled along a first plane by the single blade, wherein the single blade pivots axially about a fulcrum, wherein the fulcrum is positioned proximate to and coaxial with a turn knob shaft housed within the handle, wherein the pivoting causes a plurality of inclination angles between the blade length and the handle length, and wherein the turn knob shaft is substantially perpendicular to the handle length,
    a third predetermined path, wherein the third predetermined path comprises a third designated path traveled along a second plane by the single blade, the second plane horizontally bisecting the blade length, wherein during the travel the blade pivots axially about a handle axis while maintaining a constant angle with respect to the handle,
    a fourth predetermined path extending transversely relative to the handle length, wherein the fourth predetermined path further comprises a fourth designated path traveled along a second plane by the single blade, wherein during the travel an angle between the handle length and the blade length remains constant while the single blade moves transversely toward or away from the handle length.

11. The laryngoscope of claim 10 wherein the mechanism further comprises a finger actuated turn knob positioned at one end of the turn knob shaft.

12. The laryngoscope of claim 10 wherein the mechanism further comprises a finger actuated slider.

13. The laryngoscope of claim 10, further comprising a light source operable to project light from the laryngoscope.

14. The laryngoscope of claim 13, wherein the light source is in the handle.

15. The laryngoscope of claim 13, wherein the light source is in the blade.

16. The laryngoscope of claim 10, further comprising a camera operable to record an environment of the blade.

17. The laryngoscope of claim 16, wherein the camera is in the handle.

18. The laryngoscope of claim 16, wherein the camera is in the blade.

\* \* \* \* \*